United States Patent
Chauhan

(10) Patent No.: US 11,975,098 B2
(45) Date of Patent: May 7, 2024

(54) NANOSUSPENSIONS OF CANNABIDIOL FOR DEVELOPING WATER-DISPERSIBLE FORMULATIONS

(71) Applicant: Colorado School of Mines, Golden, CO (US)

(72) Inventor: Anuj Chauhan, Golden, CO (US)

(73) Assignee: Colorado School of Mines, Golden, CO (US)

(*) Notice: Subject to any disclaimer, the term of this patent is extended or adjusted under 35 U.S.C. 154(b) by 0 days.

(21) Appl. No.: 17/328,902

(22) Filed: May 24, 2021

(65) Prior Publication Data

US 2021/0361571 A1 Nov. 25, 2021

Related U.S. Application Data

(60) Provisional application No. 63/029,129, filed on May 22, 2020.

(51) Int. Cl.
| | | |
|---|---|---|
| *A61K 9/10* | (2006.01) | |
| *A61K 31/05* | (2006.01) | |
| *A61K 47/22* | (2006.01) | |
| *B82Y 5/00* | (2011.01) | |

(52) U.S. Cl.
CPC ............... *A61K 9/10* (2013.01); *A61K 31/05* (2013.01); *A61K 47/22* (2013.01); *B82Y 5/00* (2013.01)

(58) Field of Classification Search
CPC .......... A61K 9/10; A61K 31/05; A61K 47/22; B82Y 5/00
See application file for complete search history.

(56) References Cited

U.S. PATENT DOCUMENTS

| | | | |
|---|---|---|---|
| 7,182,950 B2 | 2/2007 | Garti et al. | |
| 8,808,734 B2 | 8/2014 | Winnicki | |
| 2005/0085409 A1* | 4/2005 | Kordikowski | B01D 11/0407 264/12 |
| 2013/0034538 A1 | 2/2013 | Garti et al. | |
| 2015/0218252 A1* | 8/2015 | Ingber | A61K 47/64 530/391.1 |
| 2020/0037638 A1* | 2/2020 | Faraci | A61K 36/185 |
| 2020/0138072 A1* | 5/2020 | Yucel | A23L 27/74 |

FOREIGN PATENT DOCUMENTS

| | | |
|---|---|---|
| EP | 3232808 | 10/2017 |
| WO | WO 2017/180954 | 10/2017 |
| WO | WO 2017/183011 | 10/2017 |

(Continued)

OTHER PUBLICATIONS

Chaumeil et al., "Micronization: a method of improving the bioavailability of poorly soluble drugs," Methods and Findings in Experimental and Clinical Pharmacology, vol. 20, No. 3, Apr. 1998, pp. 211-215. Abstract only.

(Continued)

*Primary Examiner* — Jianfeng Song
(74) *Attorney, Agent, or Firm* — Sheridan Ross P.C.

(57) ABSTRACT

Aqueous nanosuspensions of cannabidiol (CBD) having improved stability, shelf life, and/or CBD content are provided, as are methods of making such nanosuspensions. The nanosuspensions include ethyl maltol as an emulsifying agent and may be manufactured by either a melt emulsification process or a solvent evaporation process. The nanosuspensions may also have an improved taste and are thus suitable for use as, e.g., beverage additives.

4 Claims, 2 Drawing Sheets

(56) References Cited

FOREIGN PATENT DOCUMENTS

| WO | WO-2018112119 A1 * | 6/2018 | ........... A61K 31/352 |
|----|---|---|---|
| WO | WO 2019/140145 | 7/2019 | |
| WO | WO 2020/018453 | 1/2020 | |

OTHER PUBLICATIONS

Kocbek et al., "Preparation and evaluation of nanosuspensions for enhancing the dissolution of poorly soluble drugs," International Journal of Pharmaceutics, vol. 312, No. 1-2, Apr. 7, 2006, pp. 179-186.

Lindenberg et al., "Classification of orally administered drugs on the World Health Organization Model list of Essential Medicines according to the biopharmaceutics classification system," European Journal of Pharmaceutics and Biopharmaceutics, vol. 58, No. 2, Sep. 2004, pp. 265-278.

Rainbow, "Nanosuspensions in drug delivery," Nature Reviews Drug Discovery, vol. 3, Sep. 1, 2004, pp. 785-796.

Müller et al., "Chapter 17: Nanosuspensions: a formulation approach for poorly soluble and poorly bioavailable drugs," in "Handbook of Pharmaceutical Controlled Release Technology" (ed. Wise), CRC Press, 2000, pp. 345-358.

Van De Waterbeemd et al., "Part Two: Physiochemical and Biological Studies of Membrane Permeability and Oral Absorption," in "Drug Bioavailability: Estimation of Solubility, Permeability, Absorption, and Bioavailability, 2nd edition" (ed. Van De Waterbeemd), Wiley-VCH Verlag GmbH & Co., KGaA, 2008, pp. 69-220.

* cited by examiner

NANOSUSPENSIONS OF CANNABIDIOL FOR DEVELOPING WATER-DISPERSIBLE FORMULATIONS

CROSS-REFERENCE TO RELATED APPLICATIONS

This application claims the benefit of priority under 35 U.S.C. § 119(e) to U.S. Provisional Patent Application 63/029,129, filed 22 May 2020, the entirety of which is incorporated herein by reference.

FIELD OF THE INVENTION

This disclosure relates generally to water-dispersible formulations of cannabidiol (CBD), and particularly to nanosuspensions of cannabidiol with ethyl maltol.

BACKGROUND OF THE INVENTION

Oral administration is generally considered the least invasive route of drug administration and the route with the highest rate of patient compliance, and for these reasons about 84% of all medications are taken orally. However, for orally administered drugs to have a therapeutic effect, the drug must be absorbed through the intestinal walls into the bloodstream, which generally requires the drug to be water-soluble; thus, poorly water-soluble drugs generally have low bioavailability when administered orally. The bioavailability of certain drugs, particularly drugs Biopharmaceutics Classification System (BCS) Class II drugs characterized by low solubility and high permeability, can therefore be enhanced by reducing a particle size of the drug to improve the drug's rate of dissolution in water.

Drug micronization is often used to reduce drug particles to sizes on the order of between about 1 micron and about 10 microns, and techniques such as antisolvent precipitation have previously been used to create drug nanoparticles, which can be suspended in an aqueous phase to form a colloidal nanosuspension. Such colloidal nanosuspension have promise for increasing bioavailability due to their small (sub-micron) particle sizes; the Ostwald-Freundlich equation predicts that saturation solubility increases with decreased particle size (with a particularly noticeable effect for particle diameters of less than 1 micron), and this increase, together with the resulting increase in the particles' surface area-volume ratio, has been theoretically predicted and experimentally shown to significantly increase dissolution rates. However, techniques such as antisolvent precipitation often create chemically or physically unstable formulations, which frequently require organic (i.e. non-aqueous) solvents that may be difficult to completely remove. For hydrophobic drugs that are solid at room temperature, this problem can be mitigated by forming colloidal suspensions via the highly reproducible and scalable process of melt emulsification, in which the drug is melted and then emulsified in a solvent, typically water, using suitable surfactants; the emulsion is then cooled to yield a suspension of the drug in water.

Recent changes in United States laws and regulations have sparked a boom in the *cannabis* industry. Particularly, while compositions containing the principal psychoactive agent in *cannabis*, $\Delta^9$-tetrahydrocannabinol (THC), are still tightly regulated and controlled, substantially THC-free compositions containing cannabidiol (CBD) have gained much wider legal and social acceptance. Recent estimates place annual sales of CBD compositions at $390 million and forecast rapid growth to a value of $1.3 billion annually by 2022. This strong and increasing demand for CBD compositions is driven by widespread recognition of CBD's usefulness in a variety of therapeutic applications, including as an anti-inflammatory, a pain reliever, and an anxiolytic. The use of CBD compositions in the treatment of anxiety, which afflicts over 15 million Americans, has important advantages relative to conventional medication regimens, including fewer side effects and low or no risk of drug withdrawal if and when treatment ceases. Research into CBD is ongoing and many researchers have identified numerous other potential therapeutic uses for CBD.

Before being incorporated into edible products, CBD compositions for oral administration are often provided as oils (e.g. for sublingual administration) or isolate powders. However, CBD in pure form (whether as an oil or a powder) has a powerfully bitter and earthy flavor that most users find unpleasant. In addition, because CBD is hydrophobic and poorly water-soluble, it suffers from the same issues related to bioavailability as other such drugs when administered orally; the maximum theoretical bioavailability of orally administered CBD is 19%, and in most formulations bioavailability is considerably lower. Thus, given the ease of administration and appeal to users of oral formulations, much attention has been devoted to methods of forming nanosuspensions of CBD in water, which address both of these drawbacks; such nanosuspensions are often referred to in the *cannabis* industry as "water-soluble" CBD, but are more accurately termed "water-dispersible" CBD.

Because CBD is a solid at room temperature, melt emulsification is a potentially useful approach for forming nanosuspensions of CBD, but creation of chemically and physically stable aqueous nanosuspensions of CBD via melt emulsification has proven challenging. Particularly, it is difficult to provide a suitable surfactant and/or a suitable amount of a surfactant that stabilizes the suspension, is biocompatible for oral administration to a subject, and has a flavor acceptable to the subject and/or masks the unpleasant flavor of CBD to a degree acceptable to the subject.

There is thus a need in the art for chemically and physically stable aqueous nanosuspensions of CBD that include a biocompatible surfactant with an acceptable flavor and/or flavor-masking effect.

SUMMARY OF THE INVENTION

It is one aspect of the present invention to provide an aqueous nanosuspension of cannabidiol (CBD), comprising between about 0.25 wt % and about 0.75 wt % CBD; between about 0.125 wt % and about 0.75 wt % ethyl maltol; at least about 8 wt % non-ionic surfactant; and an aqueous solvent.

In certain embodiments, the non-ionic surfactant may comprise a poloxamer.

In certain embodiments, the aqueous nanosuspension may be stable at room temperature for at least about one month.

In certain embodiments, a particle size of the CBD may be less than about 100 nanometers.

In certain embodiments, a polydispersity index of the aqueous nanosuspension may be no more than about 0.3.

In certain embodiments, the aqueous nanosuspension may comprise at least about 2% CBD on a dry weight basis.

It is another aspect of the present invention to provide a method for making a composition comprising cannabidiol (CBD), the method comprising (a) combining CBD, ethyl maltol, a non-ionic surfactant, and an aqueous solvent to form a mixture; and (b) heating the mixture to melt at least the CBD to form an aqueous nanosuspension, wherein the aqueous nanosuspension comprises between about 0.25 wt % and about 0.75 wt % CBD, between about 0.125 wt % and about 0.75 wt % ethyl maltol, and at least about 8 wt % non-ionic surfactant.

In certain embodiments, the method may further comprise, following step (b), at least one of sonicating the mixture and cooling the mixture.

In certain embodiments, the non-ionic surfactant may comprise a poloxamer.

In certain embodiments, the aqueous nanosuspension may be stable at room temperature for at least about one month.

In certain embodiments, a particle size of the CBD in the aqueous nanosuspension may be less than about 100 nanometers.

In certain embodiments, a polydispersity index of the aqueous nanosuspension may be no more than about 0.3.

In certain embodiments, the method may further comprise, after step (b), lyophilizing the aqueous nanosuspension to form a dried CBD composition.

It is another aspect of the present invention to provide a method for making a composition comprising cannabidiol (CBD), the method comprising (a) dissolving CBD in an organic solvent to form an initial solution; (b) adding ethyl maltol, a non-ionic surfactant, and an aqueous solvent to the initial solution to form a mixture; and (c) evaporating the organic solvent to form an aqueous nanosuspension, wherein the aqueous nanosuspension comprises between about 0.25 wt % and about 0.75 wt % CBD, between about 0.125 wt % and about 0.75 wt % ethyl maltol, and at least about 8 wt % non-ionic surfactant.

In certain embodiments, the organic solvent may comprise dichloromethane.

In certain embodiments, the non-ionic surfactant may comprise a poloxamer.

In certain embodiments, the aqueous nanosuspension may be stable at room temperature for at least about one month.

In certain embodiments, a particle size of the CBD in the aqueous nanosuspension may be less than about 100 nanometers.

In certain embodiments, a polydispersity index of the aqueous nanosuspension may be no more than about 0.3.

In certain embodiments, the method may further comprise, after step (c), lyophilizing the aqueous nanosuspension to form a dried CBD composition.

The advantages of the present invention will be apparent from the disclosure contained herein.

As used herein, "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B, and C together.

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The embodiments and configurations described herein are neither complete nor exhaustive. As will be appreciated, other embodiments of the invention are possible utilizing, alone or in combination, one or more of the features set forth above or described in detail below.

DETAILED DESCRIPTION OF THE INVENTION

Figure 1:
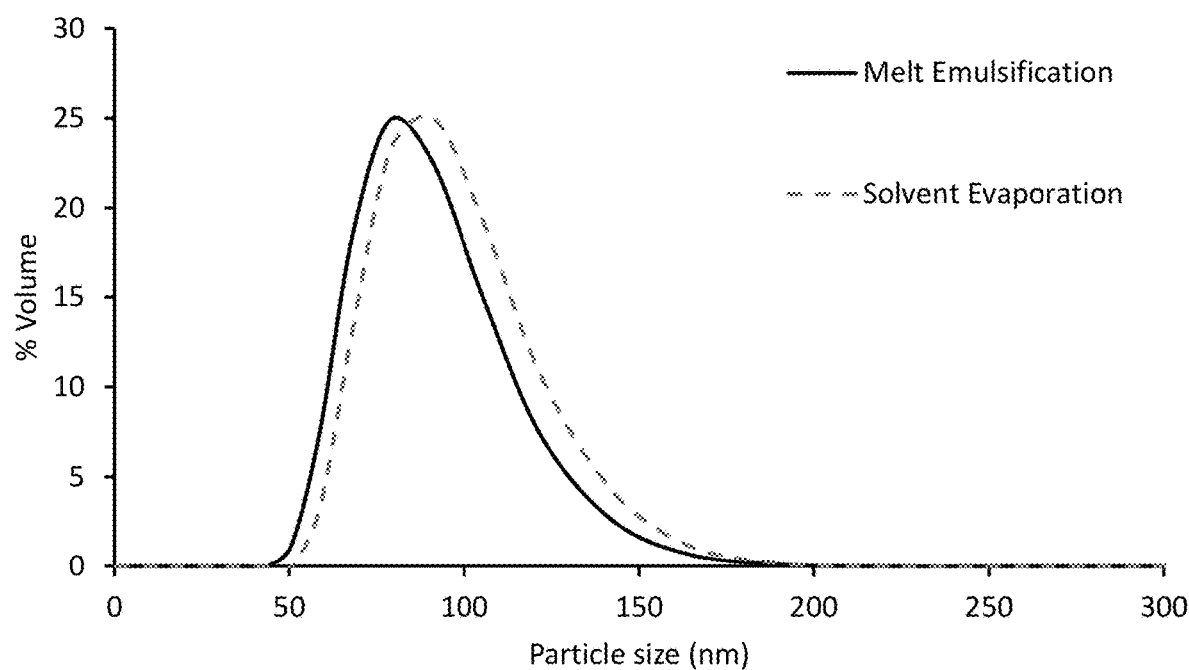
FIG. 1 is a graph comparing cannabidiol (CBD) particle size distributions in nanodispersions formed by melt emulsification and solvent evaporation.

Unless defined otherwise, all technical and scientific terms used herein have the same meaning as is commonly understood by one of ordinary skill in the art. All patents, applications, published applications, and other publications to which reference is made herein are incorporated by reference in their entirety. In the event that there is a plurality of definitions for a term herein, the definition provided in the Summary of the Invention prevails unless otherwise stated.

The present invention provides novel compositions and methods for the manufacture of water-dispersible—or, as sometimes called in the *cannabis* industry, "water-soluble"—formulations of cannabidiol (CBD). Particularly, the water-dispersible CBD formulations of the present invention minimize the unpleasant taste of CBD and/or the surfactant, while simultaneously having a prolonged shelf life and an improved degree of CBD loading as compared to the water-dispersible CBD formulations of the prior art. These benefits are achieved by the use of ethyl maltol as an additive. Ethyl maltol is a common food additive that is known to be safe for human consumption and that is frequently used as a sweetener in beverages, cakes, and fruit products, but the present inventors have unexpectedly found that it is useful for improving the water dispersibility of CBD and/or the stability of the resulting CBD formulation. The use of ethyl maltol in the manufacturing method is effective over a wide range of CBD and ethyl maltol concentrations, and the resulting water-dispersible CBD formulations are chemically and physically stable over long periods and after lyophilization.

For purposes of further disclosure and to comply with applicable written description and enablement requirements, the following references generally relate to water-dispersible formulations of CBD and related compositions, devices, methods, and systems, and are hereby incorporated by reference in their entireties:

J. C. Chaumeil, "Micronization: a method of improving the bioavailability of poorly soluble drugs," 20(3) *Methods and Findings in Experimental and Clinical Pharmacology* 211 (March 1998).

R. H. Müller et al., "Nanosuspensions: a formulation approach for poorly soluble and poorly bioavailable drugs," in *Handbook of Pharmaceutical Controlled Release Technology* 345 (Donald L. Wise ed. 2000).

Marc Lindenberg et al., "Classification of orally administered drugs on the World Health Organization Model List of Essential Medicines according to the Biopharmaceutics Classification System," 58(2) *European Journal of Pharmaceutics and Biopharmaceutics* 265 (September 2004).

Barrett E. Rainbow, "Nanosuspensions in drug delivery," 3 *Nature Reviews Drug Discovery* 785 (September 2004).

P. Kocbek et al., "Preparation and evaluation of nanosuspensions for enhancing the dissolution of poorly soluble drugs," 312(1-2) *International Journal of Pharmaceutics* 179 (April 2006).

U.S. Pat. No. 7,182,950, entitled "Nano-sized self-assembled liquid dilutable vehicles," issued 27 Feb. 2007 to Garti et al. ("Garti I"). Garti I discloses nano-sized self-assembled structured concentrates and their use as carriers of active materials.

Han van de Waterbeemd and Bernard Testa (eds.), *Drug Bioavailability: Estimation of Solubility, Permeability, Absorption, and Bioavailability* (3rd ed. 2008).

U.S. Patent Application Publication 2013/0034538, entitled "Reverse hexagonal mesophases ($H_{II}$) and uses thereof," published 7 Feb. 2013 to Garti et al. ("Garti II"). Garti II discloses reverse hexagonal mesophase ($H_{II}$) liquid crystals for formulating hydrophobic molecules.

U.S. Pat. No. 8,808,734, entitled "Cannabinoid formulations," issued 19 Aug. 2014 to Winnicki ("Winnicki"). Winnicki discloses a liposomal suspension of one or more cannabinoids or cannabinoid analogs, wherein the concentration of cannabinoids or cannabinoid analogs is 50 grams per liter and wherein a bilayer of liposomes comprises about 26% phosphatidylcholine, about 10% phosphatidylethanolamine, about 13% phosphonophospholipids, and about 1% other phospholipids.

PCT Application Publication 2017/180954, entitled "Method of making *cannabis* oil hydrophilic using emulsifiers and related cannabinoid compositions," published 19 Oct. 2017 to Silver ("Silver"). Silver discloses a method of making a hydrophilic, water-soluble *cannabis* oil by heating a base oil to a temperature of 120 to 220° F., adding *cannabis* oil to create a mixture, blending the mixture at high speed while adding an emulsifying agent, and adding water to form the composition.

PCT Application Publication 2017/183011, entitled "Water soluble cannabinoid inclusion complexes," published 26 Oct. 2017 to Degeeter et al. ("Degeeter"). Degeeter discloses a water-soluble inclusion complex comprising a cannabinoid and a β-cyclodextrin.

PCT Application Publication 2019/140,145, entitled "Transformation of cannabinol and terpene oils into water soluble dry powders for solid form sublingual delivery," published 18 Jul. 2019 to Althaus et al. ("Althaus"). Althaus discloses a composition comprising a clathrate compound including guest molecules and carrier molecules trapping the guest molecules, wherein the carrier molecules are saccharides and the guest molecules include at least one cannabinoid or terpene, and wherein the guest molecules comprise at least 18% by weight of the clathrate compound.

PCT Application Publication 2020/018453, entitled "Water-soluble cannabidiol," published 23 Jan. 2020 to Mallia et al. ("Mallia"). Mallia discloses a composition for oral consumption comprising methylated-β-cyclodextrin, cannabidiol, and water, wherein the cannabidiol is present in an amount from about 20 mg to about 40 mg per gram of methylated-β-cyclodextrin and in an amount from about 0.8 mg/mL to about 1.6 mg/mL.

European Patent 3,232,808, entitled "CBD-containing beverage," issued 1 Apr. 2020 to Steup ("Steup"). Steup discloses a CBD-containing liquid formulation, particularly a beverage containing at least one emulsifier.

The following disclosed Examples illustrate and describe various embodiments and features of the present invention.

Example 1

Suspensions of cannabidiol (CBD) were made by adding CBD (Infinite CBD, Lakewood, CO) to Dulbecco's phosphate buffer saline (PBS, Sigma-Aldrich) in a 5 mL scintillation vial. These suspensions were heated to 75° C. to melt the CBD, whereupon a 15% solution of Pluronic F68 (poloxamer 188, Sigma-Aldrich) was added until a desired concentration was obtained. The suspension was then immediately sonicated for 60 seconds and allowed to cool to room temperature.

Separately, solutions of CBD were prepared by solubilizing CBD in 200 μL of dichloromethane (DCM), then adding PBS and Pluronic as above and sonicating for 60 seconds. These solutions were left uncapped overnight to allow the DCM solvent to evaporate.

The resulting nanosuspensions were visually observed to determine whether the nanosuspension was visibly transparent (i.e. a microemulsion), translucent, or opaque. The particle size distribution was also measured at room temperature by dynamic light scattering (DLS, Malvern Nano-ZS).

Several nanosuspensions which formed transparent solutions were lyophilized by placement in a freezer at −80° C. for several hours and subsequent drying in a vacuum chamber. It is believed that the only chemical component removed by lyophilization was water. The dried samples were rehydrated by adding PBS to match the initial component concentration, and the rehydrated suspensions were analyzed for particle size distribution by DLS.

The solid components of the melt-emulsified nanosuspensions rapidly melted when the mixtures of the drug, additive, and water were heated above the highest melting point of the mixture (i.e. to at least 66° C., the melting point of CBD). For all samples, whether the system would form a visually transparent nanosuspension was evident within the first 15 minutes after sonication—no system that was not visibly transparent after 15 minutes formed a stable microemulsion, even after prolonged mixing. Table 1 gives the formulations that were prepared with various amounts of CBD, ethyl maltol, and surfactant, and expresses the initial stability and shelf life, particle size, and polydispersity index (PDI) for each emulsion.

TABLE 1

| CBD wt % | Ethyl maltol wt % | Surfactant wt % | Method | Stable? | Shelflife | Particle size (nm) | PDI |
|---|---|---|---|---|---|---|---|
| 0.5 | 0 | 1 | Melt | No | None | — | — |
| 1 | 0 | 1 | Melt | No | None | — | — |
| 0.25 | 0.25 | 1 | Melt | No | None | — | — |
| 0.375 | 0.125 | 1 | Melt | No | None | — | — |
| 0.375 | 0.125 | 1 | Solv. evap. | No | None | — | — |
| 0.25 | 0.75 | 1 | Melt | No | None | — | — |
| 0.5 | 0.5 | 1 | Melt | No | None | — | — |
| 0.75 | 0.25 | 1 | Melt | No | None | — | — |
| 0.5 | 0 | 2 | Melt | No | None | — | — |

TABLE 1-continued

| CBD wt % | Ethyl maltol wt % | Surfactant wt % | Method | Stable? | Shelflife | Particle size (nm) | PDI |
|---|---|---|---|---|---|---|---|
| 1 | 0 | 2 | Melt | No | None | — | — |
| 0.25 | 0.25 | 2 | Melt | No | None | — | — |
| 0.375 | 0.125 | 2 | Melt | No | None | — | — |
| 0.25 | 0.75 | 2 | Melt | No | None | — | — |
| 0.5 | 0.5 | 2 | Melt | No | None | — | — |
| 0.75 | 0.25 | 2 | Melt | No | None | — | — |
| 0.75 | 0.25 | 2 | Solv. evap. | No | None | — | — |
| 0.5 | 0 | 4 | Melt | No | None | — | — |
| 1 | 0 | 4 | Melt | No | None | — | — |
| 0.25 | 0.25 | 4 | Melt | No | None | — | — |
| 0.25 | 0.25 | 4 | Solv. evap. | No | None | — | — |
| 0.375 | 0.125 | 4 | Melt | No | None | — | — |
| 0.25 | 0.75 | 4 | Melt | No | None | — | — |
| 0.5 | 0.5 | 4 | Melt | No | None | — | — |
| 0.75 | 0.25 | 4 | Melt | No | None | — | — |
| 0.5 | 0 | 6 | Melt | No | None | — | — |
| 1 | 0 | 6 | Melt | No | None | — | — |
| 0.25 | 0.25 | 6 | Melt | No | None | — | — |
| 0.375 | 0.125 | 6 | Melt | No | None | — | — |
| 0.25 | 0.75 | 6 | Melt | No | None | — | — |
| 0.5 | 0.5 | 6 | Melt | No | None | — | — |
| 0.5 | 0.5 | 6 | Solv. evap. | No | None | — | — |
| 0.75 | 0.25 | 6 | Melt | No | None | — | — |
| 0.5 | 0 | 10 | Melt | No | None | — | — |
| 0.75 | 0 | 10 | Melt | No | None | — | — |
| 1 | 0 | 10 | Melt | No | None | — | — |
| 0.25 | 0.25 | 10 | Melt | Yes | >6 months | 89 ± 1 | 0.20 |
| 0.375 | 0.125 | 10 | Melt | Yes | >6 months | 95 ± 9 | 0.13 |
| 0.25 | 0.75 | 10 | Melt | Yes | >6 months | 86 ± 1 | 0.22 |
| 0.25 | 0.75 | 10 | Solv. evap. | Yes | >6 months | 91 ± 2 | 0.24 |
| 0.5 | 0.5 | 10 | Melt | Yes | >6 months | 86 ± 1 | 0.18 |
| 0.75 | 0.25 | 10 | Melt | Yes | ~1 month | 141 ± 12 | 0.18 |
| 0.8 | 0.2 | 10 | Melt | Yes | <2 days | 204 ± 12 | 0.20 |
| 0.875 | 0.125 | 10 | Melt | Yes | <1 day | 208 ± 8 | 0.22 |
| 1 | 0.5 | 10 | Melt | No | None | — | — |
| 1.25 | 0.25 | 10 | Melt | No | None | — | — |
| 1.5 | 0.25 | 10 | Melt | No | None | — | — |
| 1.5 | 0.5 | 10 | Melt | No | None | — | — |
| 1.75 | 0.25 | 10 | Melt | No | None | — | — |

Molten macroemulsions had poor stability when cooled to room temperature and exhibited rapid precipitation of CBD and complete phase separation within a few days of shelf storage at room temperature; most solutions were likewise unstable upon cooling. CBD is highly insoluble in aqueous solvents and, when cooled to room temperature, the nanosuspensions tend to aggregate into macroscopic particles. The addition of ethyl maltol mitigates this aggregation to stabilize the solution and has the added benefit of improving the taste of the oral composition.

At lower surfactant concentrations, CBD formulations demonstrate no stability, and none except the 10 wt % surfactant formulations formed a stable emulsion. Likewise, no formulation without ethyl maltol formed a stable solution. In all unstable emulsions, at least one component precipitated out of solution and formed a solid sediment; without wishing to be bound by any particular theory, it is hypothesized that the absence of ethyl maltol and low surfactant concentrations allow particles to flocculate, resulting in sedimentation. Solutions comprising 0.8 wt % or 0.875 wt % CBD formed briefly stable emulsions that exhibited precipitation of particles of roughly 200 nm within less than two days, but as the CBD content was lowered to 0.75 wt %, the system became more stable (shelf life of about 1 month, particle size 141 nm), and as the CBD content was further lowered, the stability of the emulsion was greatly enhanced (shelf life of at least 6 months, particle size less than 100 nm). All formulations had polydispersity indices of no more than about 0.3, which is the recommended upper limit for pharmaceutical formulations.

Referring now to FIG. 1, it can be seen that the use of solvent evaporation had a minimal effect on particle size relative to melt emulsification; the particle size distributions for the two methods are nearly identical, with solvent evaporation having an average particle size approximately 5 nm larger and a similar polydispersity index. This result demonstrates that both melt emulsification and solvent evaporation can be used with ethyl maltol to reliably fabricate stable CBD emulsions.

Example 2

The five formulations of Example 1 that demonstrated significant stability after one week were reexamined by DLS after 30 days to determine any change in particle size distribution or polydispersity. Results are given in Table 2.

TABLE 2

| ID | CBD wt % | Ethyl maltol wt % | Surfactant wt % | Particle size (nm) | | PDI | |
|---|---|---|---|---|---|---|---|
| | | | | Initial | 30 days | Initial | 30 days |
| 1 | 0.25 | 0.25 | 10 | 89 ± 1 | 98 ± 2 | 0.20 | 0.23 |
| 2 | 0.375 | 0.125 | 10 | 95 ± 9 | 99 ± 1 | 0.13 | 0.21 |
| 3 | 0.25 | 0.75 | 10 | 86 ± 1 | 95 ± 1 | 0.22 | 0.22 |

TABLE 2-continued

| ID | CBD wt % | Ethyl maltol wt % | Surfactant wt % | Particle size (nm) Initial | Particle size (nm) 30 days | PDI Initial | PDI 30 days |
|---|---|---|---|---|---|---|---|
| 4 | 0.5 | 0.5 | 10 | 86 ± 1 | 91 ± 1 | 0.18 | 0.18 |
| 5 | 0.75 | 0.25 | 10 | 141 ± 12 | 115 ± 4 | 0.18 | 0.40 |

While the particle sizes and polydispersities of the Formulations 1-4 increased slightly over time, all had average particle sizes after 30 days of less than 100 nm and retained PDI of less than 0.3. Formulation 5, however, saw a decrease in particle size and a significant increase in PDI, likely suggesting aggregation and settling of larger particles. In addition to improving the flavor of the formulation, the addition of ethyl maltol had the surprising and unexpected benefit of improving the stability of the formulations; compare, for example Formulation ID 4 (0.5% CBD, 0.5% Ethyl maltol, 10% surfactant) with the 0.5% CBD, 10% surfactant formulation in Table 1.

Example 3

Prior liquid nanosuspensions of CBD, while attractive for use as concentrated compositions that can be readily and rapidly consumed, have exhibited shorter shelf life and lower concentrations than dried CBD compositions. Commercially available liquid nanosuspensions generally have a CBD concentration of about 0.1 wt %. By contrast, the present inventors have been able to obtain compositions with a shelf life of more (in some cases much more) than 30 days that can have CBD concentrations of up to five times this amount. Once such formulations are dehydrated, the concentrations of CBD, ethyl maltol, and surfactant increase significantly and can provide a stable and easily dissolvable system. The present inventors thus examined the concentrations of the lyophilized nanosuspension formulations both before and after lyophilization; the results are given in Table 3.

TABLE 3

| Formulation | | CBD wt % | Ethyl maltol wt % | Surfactant wt % |
|---|---|---|---|---|
| 1 | Liquid | 0.25 | 0.25 | 10 |
|   | Freeze-dried | 2.4 | 2.4 | 95.2 |
| 2 | Liquid | 0.375 | 0.125 | 10 |
|   | Freeze-dried | 3.6 | 1.2 | 95.2 |
| 3 | Liquid | 0.25 | 0.75 | 10 |
|   | Freeze-dried | 2.3 | 6.8 | 90.9 |
| 4 | Liquid | 0.5 | 0.5 | 10 |
|   | Freeze-dried | 4.55 | 4.55 | 90.9 |
| 5 | Liquid | 0.75 | 0.25 | 10 |
|   | Freeze-dried | 6.8 | 2.3 | 90.9 |

Figure 2A:
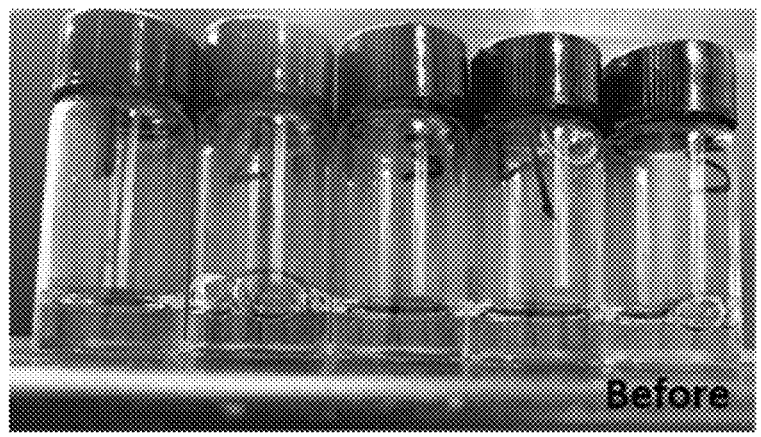
FIGS. 2A, 2B, and 2C are photographs of melt-emulsified CBD formulations according to the present invention as an aqueous nanodispersion, after lyophilization, and after post-lyophilization redispersion, respectively.
Figure 2B:
Figure 2C:

The dried particles formed by lyophilization of the liquid nanosuspension can be pressed into tablet form, coated for protection against gastric conditions, and/or encapsulated in a gelatin composition that dissolves only at neutral or near-neutral pH (i.e. as in the small intestine), all of which are common forms for over-the-counter drugs. Additionally, the dried powders can be added to liquids at any desired concentrations to rapidly formulate CBD nanosuspensions for multiple applications. However, for dehydrated CBD compositions to maintain improved viability and rate of onset, the particles must retain favorable pharmacochemical properties once rehydrated. Table 4 illustrates the particle sizes of Formulations 1-5 before and after rehydration, and FIGS. 2A through 2C show the optical results before and after rehydration.

TABLE 4

| Formulation | Particle size (nm) Pre-rehydration | Particle size (nm) Post-rehydration | PDI Pre-rehydration | PDI Post-rehydration |
|---|---|---|---|---|
| 1 | 89 ± 1 | 102 ± 13 | 0.20 | 0.20 |
| 2 | 95 ± 9 | 117 ± 9 | 0.13 | 0.15 |
| 3 | 86 ± 1 | 93 ± 16 | 0.22 | 0.22 |
| 4 | 86 ± 1 | 103 ± 12 | 0.18 | 0.14 |
| 5 | 141 ± 12 | 177 ± 4 | 0.18 | 0.41 |

Formulations 1-4 all retained favorable optical quality, having a visual appearance after rehydration similar to that before rehydration; additionally, while lyophilization and rehydration resulted in a slight increase in particle size, the effect on PDI was negligible. Formulation 5, by contrast, exhibited a significant optical degradation, forming a slightly opaque solution upon rehydration, and significant increases in particle size and PDI were observed.

Example 4

One advantage of the present invention is that, although the CBD content on a per-weight basis can be up to at least about five times that of conventional CBD compositions, the compositions may be diluted by a consumer to any desired degree, e.g. by mixing the aqueous nanosuspensions of the invention with a beverage to provide a CBD additive or enhancement. Thus, the present inventors investigated the behavior of the CBD compositions of the present invention by diluting the nanosuspensions by a factor of 5 with water and observing any apparent change in the properties of the nanosuspension after 5 minutes. The results are given in Table 5.

TABLE 5

| Formulation | Particle size (nm) Pre-dilution | Particle size (nm) Post-dilution | PDI Pre-dilution | PDI Post-dilution |
|---|---|---|---|---|
| 1 | 89 ± 1 | 163 ± 4 | 0.20 | 0.32 |
| 2 | 95 ± 9 | 196 ± 11 | 0.13 | 0.30 |
| 3 | 86 ± 1 | 178 ± 4 | 0.22 | 0.13 |
| 4 | 86 ± 1 | 205 ± 4 | 0.18 | 0.12 |
| 5 | 141 ± 12 | 225 ± 3 | 0.18 | 0.17 |

These results demonstrate that formulations with lower overall CBD loading, such as Formulations 1 and 2, show approximately a doubling of particle size and a significant increase in polydispersity. For formulations with higher CBD loading, dilution again approximately doubled average particle size (except in Formulation 5, in which particle size increased by about 60%), but polydispersity tended to decrease instead. Thus, although dilution does result in significantly increased particle size, the particle sizes tend to remain within acceptable limits that maintain the improved bioavailability over pure isolate products, and the diluted solutions can still be easily consumed by a user. Meanwhile, the more favorable PDI behavior of higher-CBD compositions can be leveraged for use as a more suitable flavor enhancer or additive than other commercially available CBD additives.

The invention illustratively disclosed herein suitably may be practiced in the absence of any element which is not specifically disclosed herein. It is apparent to those skilled in the art, however, that many changes, variations, modifications, other uses, and applications of the invention are possible, and also changes, variations, modifications, other uses, and applications which do not depart from the spirit and scope of the invention are deemed to be covered by the invention, which is limited only by the claims which follow.

The foregoing discussion of the invention has been presented for purposes of illustration and description. The foregoing is not intended to limit the invention to the form or forms disclosed herein. In the foregoing Detailed Description of the Invention, for example, various features of the invention are grouped together in one or more embodiments for the purpose of streamlining the disclosure. The features of the embodiments of the invention may be combined in alternate embodiments other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description of the Invention, with each claim standing on its own as a separate preferred embodiment of the invention.

Moreover, though the description of the invention has included description of one or more embodiments and certain variations and modifications, other variations, combinations, and modifications are within the scope of the invention, e.g. as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

The invention claimed is:

1. An aqueous nanosuspension of cannabidiol (CBD), consisting of:
   between about 0.25 wt % and about 0.75 wt % CBD;
   between about 0.125 wt % and about 0.75 wt % ethyl maltol;
   at least about 8 wt % non-ionic surfactant; and
   an aqueous solvent,
   wherein the aqueous nanosuspension is stable at room temperature for at least about one month and a particle size of the CBD is less than about 100 nanometers.

2. The aqueous nanosuspension of claim 1, wherein the non-ionic surfactant comprises a poloxamer.

3. The aqueous nanosuspension of claim 1, wherein a polydispersity index of the aqueous nanosuspension is no more than about 0.3.

4. The aqueous nanosuspension of claim 1, comprising at least about 2% CBD on a dry weight basis.

* * * * *